United States Patent [19]

Kolstad et al.

[11] Patent Number: 4,973,449

[45] Date of Patent: Nov. 27, 1990

[54] STERILIZATION METHOD

[75] Inventors: Robert A. Kolstad, Mesquite, Tex.; Robert R. Runnells, Kaysville, Utah; John C. Schmoegner, Redondo Beach, Calif.

[73] Assignee: MDT Corporation, Torrance, Calif.

[21] Appl. No.: 837,724

[22] Filed: Mar. 10, 1986

[51] Int. Cl.⁵ ............................................. A61L 2/20
[52] U.S. Cl. ...................................... 422/27; 422/28; 422/33; 422/36
[58] Field of Search .................... 422/28, 33, 36, 27

[56] References Cited

U.S. PATENT DOCUMENTS

| | | |
|---|---|---|
| 4,169,123 | 9/1979 | Moore et al. |
| 4,169,124 | 9/1979 | Forstrom et al. |
| 4,230,663 | 10/1980 | Forstrom et al. ........... 422/33 |
| 4,447,394 | 5/1984 | Krouther ..................... 422/33 |

FOREIGN PATENT DOCUMENTS

| | | | |
|---|---|---|---|
| 2921915 | 12/1980 | Fed. Rep. of Germany | 422/33 |
| 2544615 | 10/1984 | France | 422/36 |

Primary Examiner—Robert J. Warden
Assistant Examiner—Jill Johnston
Attorney, Agent, or Firm—Trask, Britt & Rossa

[57] ABSTRACT

Heat-labile articles are sterilized by subjecting them to pulses of sporicidal vapors and maintaining them for a holding period in contact with such vapors.

37 Claims, 2 Drawing Sheets

STERILIZATION METHOD

BACKGROUND OF THE INVENTION

1. Field:

This invention relates to sterilization and is specifically directed to the sterilization of heat-labile, medical and dental devices, instruments, and materials.

2. State of the Art:

Rapid recirculation of packaged or loose instruments is a highly desired objective of modern medical and dental practices. Methods for sterilizing heat-labile medical instruments are known, but none of the methods currently practiced fulfills all major requirements. Ethylene oxide gas treatment provides adequate sterilization, but requires a lengthy aeration period following treatment, in order to remove absorbed chemicals from porous materials. Instruments packaged in accordance with modern techniques cannot be submerged in liquids such as glutaraldehyde. Liquid sterilization of unpackaged instruments imposes the requirements of post-treatment rinsing and direct handling, both of which carry the risk of recontamination. Formaldehyde gas has been utilized as a disinfectant. It has long been understood, however, that formaldehyde gas is practical as a sterilant only at elevated temperatures and pressures. It is generally understood that sterilization by most methods is enhanced by increasing the temperature of the sterilization medium. The necessity for relatively low temperatures thus complicates the problem of sterilizing heat-labile instruments. It is also generally recognized that the efficacy of gas sterilization is characteristically decreased at lower pressures. The construction of high pressure vessels is relatively expensive, however, and the long term operation and maintenance of such vessels can be costly.

Gunnar Nordgren reported certain work done with gaseous formaldehyde under so-called "pulsing" conditions. Nordgren applied a vacuum to a sterilization chamber and periodically introduced air passed through aqueous formaldehyde (formalin) into the chamber. Each introduction of gas may be regarded as a "pulse." The pressure conditions within the chamber thus fluctuated between an established upper value and a reduced level. According to the procedure used by Nordgren, a vacuum pump was continuously operated so that as soon as formaldehyde gas was introduced to the chamber, the pressure within the chamber commenced its downward cycle. Nordgren found that repeated passages of air through heated formalin (37% by volume formaldehyde in aqueous solution) into the evacuated chamber warmed to 60° C. was effective in destroying spores of *Bacillus anthracis* or *Bacillus subtilis* dried onto rubber. This work, as well as a description of related investigations up through the year 1939, is contained in a historical review, "Investigations on the Sterilization Efficacy of Gaseous Formaldehyde," by Gunnar Nordgren, publisher Einar Munksgaard, Copenhagen, 1939.

The biological indicators required under modern practice by the Environmental Protection Agency in its "Licensure Protocol" are set forth, for example, in Sporicidal Test (4) of the "Official Methods of Analysis" of the Association of Official Analytical Chemists, Washington, D.C., 13th Ed., 1980, Horowitz, AOAC Methods (1980). These indicators are considerably more difficult to sterilize with formaldehyde gas than are the aforementioned biological indicators utilized by Nordgren. The techniques taught by Nordgren have not demonstrated acceptable sporicidal activity of formaldehyde gas in accordance with AOAC Methods (1980).

There remains a need for an effective method for sterilizing heat-labile and other packaged instruments for which high temperature or liquid sterilization techniques are impractical or otherwise unsuitable. Although other sporicidal gasses are known, the sterilizing gas of choice is formaldehyde because of its familiarity, availability, and relative safety.

SUMMARY OF THE INVENTION

The present invention provides a method for sterilizing objects, notably heat-labile objects, contaminated with microorganisms. The method involves placing the objects to be sterilized in a sterilizing chamber and then subjecting those objects alternately to relatively low and relatively high pressures in the presence of a sporicidal atmosphere. Thereafter, the objects are held in the sporicidal atmosphere at relatively high pressures for a prescribed "holding period." As used in this disclosure, a "pulsing period" and "holding period" together comprise a "cycle." The sterilizing procedure ordinarily will comprise a plurality of such cycles.

Although the procedures of this invention have some applicability under high temperature conditions, either with or without steam, the practical embodiments contemplated by this invention involve sterilizing treatments at relatively low temperatures, ordinarily within the range of about 120° F. to about 160° F., usually below about 140° F., in the presence of chemical vapors, notably a mixture whose active ingredients are formaldehyde (or equivalent), alcohols and water. Certain inert constituents, such as denaturing ingredients, may also be present.

The method of this invention is practiced in a sterilization chamber such as a metal cylinder with a loading door and heating jacket or other means for maintaining a relatively uniform temperature within the chamber. The chamber is associated with a pump for reducing the pressure within the chamber to relatively high vacuums; e.g., in excess of 20 inches/Hg (about 5 psi). The chamber is also associated with means for providing pulses of gas during a pulsing period. These pulsing means typically include a pump, a gas generator connected to the chamber through a pulse valve and a metering system for delivering premeasured volumes of sterilization fluid to the gas generator.

Certain embodiments utilize a separate high pressure chamber as a gas generator. The volume of the gas generator chamber is then correlated to the volume of the sterilization chamber to deliver the prescribed biocidal atmosphere to the interior of the sterilizing chamber during each pulse. The pressure and temperature conditions desired for the sterilization procedure provide the design parameters for the gas generator chamber. The necessary quantity of biocidal liquid is heated within the gas generator to the temperature which results in the desired conditions (pressure, temperature, level of atomization, etc.) within the sterilization chamber. The heat carried by the biocidal vapor introduced to the sterilizing chamber is taken into consideration as well as the conditions under which the biocidal vapors may tend to condense to form residues at the end of the sterilization procedure. While condensation and residues are undesirable, it is necessary to introduce an efficacious quantity of the biocidal vapors to the sterilization chamber. The amount of liquid vaporized within the gas generator is thus determined with these factors in mind. The precise quantities, temperatures and volume ratios appropriate in any given instance can be determined through the application of well known physical relationships, including the ideal gas law ($PV=nRT$) and an empirical determination of the effective biocidal concentration of the particular biocidal formulation selected for use.

A pulsing period may be divided into any convenient number of pulses, the precise number being a function of the equipment available for this purpose, among other factors. It is generally preferred to maximize the number of pulses occurring during a pulsing period. A pulse- is initiated by introducing sterilizing vapors to the previously evacuated sterilization chamber. A pulse terminates when the pressure within the chamber elevates to or near the selected maximum sterilization pressure of the sterilization procedure. At the termination of a pulse, the sterilization chamber is again isolated from the source of chemical vapors, and it is again evacuated to or near the preselected minimum sterilization pressure of the sterilization procedure. The next pulse is initiated by again introducing sterilizing vapors to the sterilizing chamber. Pulsing is continued in this fashion throughout the pulsing period. At the end of the pulse period, the vapors introduced during the final pulse are maintained within the chamber at elevated pressure during a holding period of prescribed duration to complete a pulse-hold cycle.

Sterilization procedures characterized by various numbers of cycles, including various relationships of pulsing periods and holding periods, are within contemplation. Because the sterilization conditions found most efficacious for particular objects may differ, it is conceivable that in certain instances, a sterilization procedure may include cycles dissimilar from each other. Differing relationships between the durations of pulsing periods and holding periods, respectively, may be desirable under some circumstances. It is presently regarded as preferable practice to divide a sterilization procedure into at least two cycles. The holding period within each cycle should comprise a significant portion, for example one-third, of the total duration of the cycle. Holding periods less than one-fourth the duration of a preceding pulsing period are usually inadequate in practice.

For a one hour sterilization procedure, a presently preferred practice is to divide the procedure into four cycles, each with a pulsing period of 10 minutes followed by a holding period of five minutes. This practice achieves better results than does a pulsing period of 40 minutes followed by a holding period of 20 minutes. In general, within practical limits of the equipment available, it is preferred to maximize the number of pulses during each pulsing period. For example, 20 discrete pulses within a two minute pulsing period is considered preferable to 10 discrete pulses during the same two minute pulsing period.

Although it is generally considered that higher pressures enhance the killing efficiencies of most sterilization procedures, the pressure differential experienced between the lowest pressure and highest pressure of each pulse, as well as the pressure differential between the pressure at the initiation of the pulse and the pressure maintained during the holding period, is of primary importance to the present invention. It is preferred to conduct the procedure of this invention at the highest temperature tolerable to the materials being subjected to sterilization. Ordinarily, these temperatures will be below about 160° F., the most practical range being considered to be between about 120° F. and 140° F.

For a variety of environmental, economical and practical reasons, it is desirable to recycle the sterilizing atmosphere withdrawn from the sterilizing chamber at the end of each pulse for reintroduction at the commencement of subsequent pulses. It is also necessary to purge the sterilization chamber of residual vapors at the end of a procedure and to remove the atmospheric air from the chamber at the initiation of a procedure. Thus, the vacuum pump is ideally provided with means for selectively exhausting the initial atmosphere contained by the sterilization chamber from the system and thereafter recycling sterilizing atmosphere between the chamber and the generator system utilized for introducing sterilizing vapors to the chamber during the sterilization procedure. These means typically comprise suitable valvings, filters and piping.

The sterilization vapors of this invention may comprise any biocidal chemical which is either gaseous or vaporizable under the conditions of operation. The resulting vapor should also be stable under those conditions. The biocidal vapor of most interest at present is one comprising formaldehyde. Ideally, the process is run with the lowest concentration of formaldehyde which will yield reliable results, avoid toxicity risk to personnel, and reduce the burden of disposal procedures. When formaldehyde is utilized in this invention, it is conveniently used in the form of formalin diluted substantially, e.g. 5:1 by volume, with 3A alcohol (95% ethyl, 5% methyl alcohol by volume). Both 3A alcohol and formalin contain water. It has further been found advantageous to include a small portion of isopropyl alcohol (typically about 5% by volume of the total alcohol present in the formulation).

The method of this invention is effective in sterilizing medical apparatus for which no adequate sterilization method has previously been available. For example, endoscopes may be satisfactorily sterilized using the apparatus and procedures disclosed herein.

BRIEF DESCRIPTION OF THE DRAWINGS

In the drawings, which illustrate that which is presently regarded as the best mode for carrying out the invention.

DESCRIPTION OF THE ILLUSTRATED EMBODIMENT

Figure 1:
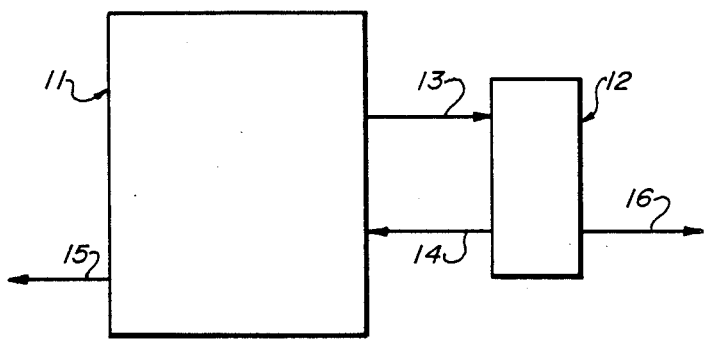
FIG. 1 is a block diagram illustrating the sterilization chamber and the gas generator required for the practice of the invention.

Referring to FIG. 1, the apparatus of this invention includes a sterilization chamber 11 and a gas generator 12 interconnected by fluid communication paths 13 and 14, respectively. In practice, the sterilization chamber 11 is ordinarily capable of withstanding a high internal vacuum but need not withstand a high internal pressure while the generator 12 is ordinarily a much smaller chamber or vessel capable of withstanding moderately elevated pressures. Means 15 are provided for evacuating the sterilization chamber 11 and other means 16 are provided for discharging spent vapors from the generator 12.

The usual procedure envisioned by this invention is to maintain the temperature in the sterilization chamber 11 at a relatively low level, typically below about 160° F. A higher temperature, for example in the range of 250° F. to 400° F., may be maintained in the generator 12 to facilitate vaporization of biocidal liquid. It is important to avoid too high a temperature in the generator 12 to avoid impacting undesirably on the temperatures inside the sterilization chamber 11.

At the commencement of a sterilization procedure, a vacuum is pulled in the chamber 11. Simultaneously, liquid is introduced to the generator 12. Ordinarily, a metered amount of liquid is introduced to generate a preselected pressure in the generator. For example, at approximately 350° F., 15 ml. of a formaldehyde solution in a generator 12 having an internal volume of approximately six liters develops a pressure of about 25 psig. in the generator 12. The communication line 14 is then opened so that vapors pass from the generator 12 to the sterilization chamber 11, thereby almost instantaneously equalizing the pressures between the two chambers. The communication path 14 is then closed and the communication path 13 is opened through a pump or other means which transfers vapors from the sterilization chamber 11 into the generator 12, thereby again to create a pressure differential between the two chambers.

This procedure constitutes a first "pulse" of the pulsing period and is repeated by alternately opening and closing the communication paths 13 and 14, respectively, to subject the contents of the sterilization chamber 11 alternately to relatively low (typically from near vacuum to about 10 inches of mercury) and relatively high (near atmospheric or above) pressures. The consequence of the procedure is to subject the contents of the sterilization chamber to pressure differential pulses of significant magnitude, typically in the range of 25 to 40 pounds per square inch, in the presence of biocidal chemical vapors.

At the end of the preselected pulsing period, the communication line 14 remains open so that the interiors of the chambers 11 and 12 are in open communication at elevated pressure. During a predetermined holding period, the cycle of pulsing and holding is repeated any desired number of times, and for the durations selected to effect adequate sterilization in a given instance.

Figure 2:
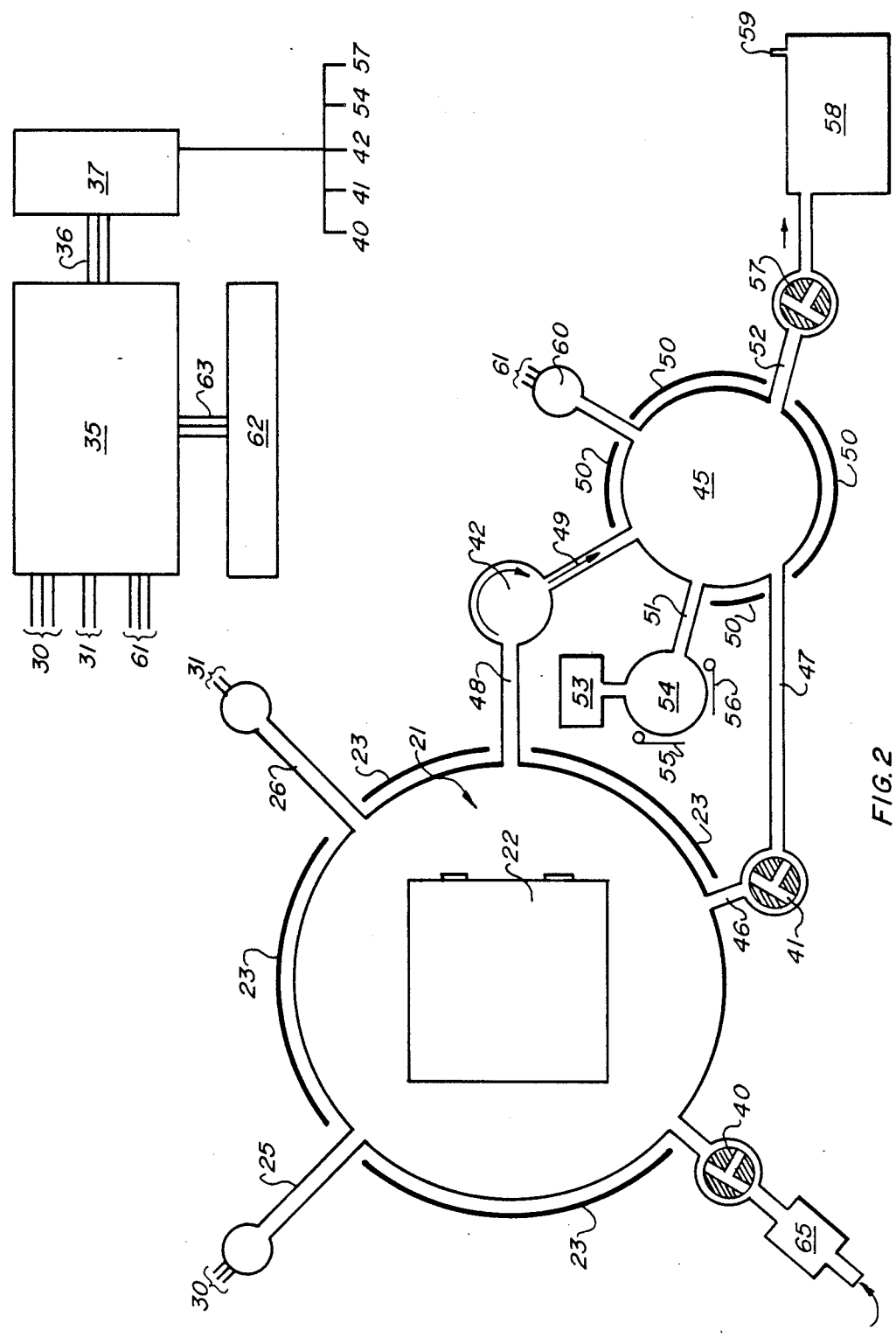
FIG. 2 is a schematic diagram of the chamber and generator of FIG. 1, together with associated apparatus comprising an assembly adapted for the practice of the invention.

The apparatus illustrated by FIG. 2 is a typical embodiment of the invention and includes a sterilization chamber 21 constructed as an aluminum rectangular vessel approximately 30 cm. high, 23 cm. wide and 60 cm. long to contain a volume of approximately 40 liters. The chamber 21 is provided with a front loading door 22 and a heating jacket 23 comprising electric heating coils rated at approximately 400 watts. The interior of the chamber 21 is monitored by a pressure sensor 25 and a temperature sensor 26. Leads 30 from the pressure sensor 25 and 31 from the temperature sensor 26 may be connected to interface circuitry 35 which in turn interfaces through appropriate conductors 36 to control circuitry 37. When the door 22 is closed, the interior of the sterilization chamber 21 is sealed. Passage of fluids to and from the interior of the chamber 21 must thus be through either the solenoid-controlled valve 40, the transfer valve 41, or the pump 42.

The sterilization chamber 21 is interconnected to a generator chamber 45 in a fluid flow loop comprising, as a first leg, the transfer valve 41 and its associated conduits 46, 47 and, as a second leg, the pump 42 and its associated conduits 48, 49. The generator 45 is a closed pressure tank of approximately six liters volume and is provided with a heating jacket 50 which may include electrical coils rated at approximately 500 watts. This chamber 45 is normally sealed and is in sealed communication with an inlet conduit 51 and an outlet conduit 52.

Sterilizing fluid is stored in a reservoir 53 from which are extracted measured quantities of such fluid for introduction through the conduit 51 to the chamber 45 through a metering valve 54. As a safety feature, the metering valve 54 is provided with limit switches 55, 56. Discharge from the generator chamber 45 through conduit 52 is through a solenoid-controlled valve 57 to a filter device 58 and eventually to the atmosphere through a port 59.

The pressure conditions within the generator are monitored by a pressure sensor 60 which includes leads 61 for connection to the interface circuitry 35. The signals delivered to interface circuitry 35 through the leads 30, 31 and 61 may be displayed by display circuitry 62 interconnected to the interface circuitry 35 by appropriate conductors 63. Each of the devices 40, 41, 42, 54 and 57 may be controlled by signals generated by the control circuitry 37 in conventional fashion. Air introduced to the chamber 21 through the solenoid valve 40 is drawn through a filter inlet 65.

Operation of the apparatus illustrated by FIG. 2 will be explained by a reference to the following examples.

EXAMPLE 1

Sterilizing apparatus was assembled as illustrated by FIG. 2. Biocidal liquid was stored in the reservoir 53. The heating jacket 23 was operated to maintain the temperature within the chamber 21 at approximately 130° F. plus or minus 5° F. The heating jacket 50 was operated to maintain the temperature within the chamber 45 at approximately 280° F. plus or minus 10° F. With the solenoid valve 40 and the transfer valve 41 closed and the solenoid valve 57 open, the pump 42 was operated to draw a vacuum in the chamber 21.

When a vacuum of eight inches of mercury had been achieved in the sterilization chamber 21, solenoid valve 57 was closed. Immediately thereafter, the metering valve 54 was operated to deposit approximately 15 ml. of sterilizing biocidal liquid into the interior of the generator 45. Vaporization of the fluid caused an increase of pressure within the generator 45. When the pressure within the generator 45 achieved a value of 18 psig., the transfer valve 41 was operated to open communication between the interiors of the chambers 21 and 45. The pump 42 remained operational so that immediately upon the transfer of vapors from the generator 45 through the conduit 46 to the interior of the chamber 21, the pump 42 commenced withdrawing the vapors through the conduit 48 and recycling the vapors through the conduit 49 to the interior of the chamber 45. The valve 41 was then closed until the internal pressure of the generator 45 again achieved a level of 18 psig., at which time the valve 41 was once again opened to permit the transfer of vapors from the generator 45 to the sterilization chamber 21.

Equalization of the pressures in the interiors of the vessels 21 and 45 is substantially instantaneous upon even a partial opening of the valve 41. In the illustrated instance, the valve 41 is a rotary valve which, once activated, requires approximately one to four seconds to rotate through open and back to closed position. Each rotation from open to closed position effects a single pressure pulse within the chamber 21. The valve 41 was continuously opened and closed as described during a pulsing period of 10 minutes.

The transfer valve 41 was then rotated to open position, the pump 42 was stopped, and the interior of the chamber 21 was held at the resulting pressure (approximately atmospheric) for a period of five minutes. The transfer valve 41 was then rotated to closed position, the pump 42 was again started, and when the pressure within the generator chamber 45 again achieved 18 psig., the transfer valve 41 was again opened and the pulsing and holding cycle was repeated until a total of four such cycles had been completed within an elapsed time of approximately 60 minutes.

Solenoid valves 40 and 57 were then opened, and the pump was operated to purge the contents of both chambers 21 and 45 by drawing atmospheric air through the filter 65 and the valve 40 through the chambers 21, 45 out through the conduit 52 and the valve 57, eventually exiting to the atmosphere through filter 58 and exhaust port 59. This purge was maintained for approximately 10 minutes, after which the solenoid valve 57 was closed, and the pump 42 was stopped.

EXAMPLE 2

Various biocidal liquids were prepared as reported in Table A below.

TABLE A

| Formulation | Vol. Percent Formalin[1] | Vol. Percent Isopropyl Alcohol[2] | Vol. Percent 3A Alcohol[3] |
|---|---|---|---|
| I | 50 | 50 | — |
| II | 16⅔ | 4 | 79¼ |
| III | 75 | 25 | — |
| IV | 25 | 75 | — |

[1]Commercial-grade formalin (37% formaldehyde, 12% methanol in water by volume).
[2]Commercial-grade isopropyl alcohol (99%).
[3]Commercial-grade 3A alcohol (95% ethyl alcohol (190 proof), 5% methyl alcohol (99%), by volume).

Each of Formulations I, II, III, and IV was utilized in a sterilization efficacy test, utilizing a procedure similar to that described in Example 1. Biological indicators were prepared in accordance with the methodology prescribed by Sporicidal Test (4), AOAC Methods (1980). Each formulation was determined to be effective; that is, all of the indicators challenged (80 to 120 for each formulation) were sterilized. By comparison, a challenge of similar biological indicators at about 160° F. for six hours by exposure to formalin gas generated from 15 mls. of liquid and allowed to diffuse into the same sterilization chamber was ineffective. (It failed to sterilize any of 50 indicators.)

EXAMPLE 3

Formulation I was utilized in the equipment described by Example 1 in accordance with the procedures of that example, except that cycles of different duration were followed to construct various sterilization procedures. The programs and effectiveness of several sterilization procedures are reported in Table B. Sporicidal effectiveness was determined in each instance by challenging 100 biological indicators prepared in accordance with Sporicidal Test (4), AOAC Methods (1980). The pressure in the sterilizer during the holding periods was approximately atmospheric.

TABLE B

| Pulse Period (minutes) | Holding Period (minutes) | Number of Cycles | Total Time | Survivors/Killed |
|---|---|---|---|---|
| 7 | 3 | 1 | 10 | 8/92 |
| 14 | 6 | 1 | 20 | 2/98 |
| 10 | 5 | 4 | 60 | 0/100 |
| 20 | 10 | 2 | 60 | 0/100 |

Reference in the specification, including the examples, to details of certain specific embodiments is not intended to restrict the scope of the appended claims which themselves recite those details regarded as important to the invention.

We claim:

1. A method of sterilizing objects contaminated with microorganisms comprising:
   placing the objects in a sterilizing chamber and subjecting them to a sporicidal atmosphere which is unsaturated with respect to water; while
   subjecting said objects alternately to relatively low and relatively high pressure conditions during a pulsing period; and
   thereafter holding said objects in said atmosphere at a relatively high pressure for a holding period.

2. A method according to claim 1 wherein said sporicidal atmosphere is maintained at a temperature within the range of about room temperature to about 160° F.; and the pressure within said sterilizing chamber during said pulsing period varies in magnitude by about 25 to about 40 psi.

3. A method according to claim 1 including a plurality of pulsing periods alternating with a plurality of holding periods.

4. A method according to claim 3 wherein each said holding period has a duration of at least about one-fourth the duration of the preceding said pulsing period.

5. A method according to claim 1 wherein said sporicidal atmosphere is produced by vaporizing a sterilizing fluid comprising formaldehyde, alcohol and water.

6. A method according to claim 5 wherein said sporicidal atmosphere is maintained at a temperature within the range of about 120° to about 140° F.

7. A method according to claim 6 wherein during said pulsing period, the pressure is caused to increase from said relatively low pressure to said relativing high pressure substantially instantaneously.

8. A method according to claim 7 wherein said low pressure is less than about 10 inches of Hg and said high pressure is at least about atmospheric.

9. A method according to claim 1 wherein said sporicidal atmosphere comprises formaldehyde, alcohol and water, and is unsaturated with respect to water.

10. A method according to claim 9 wherein said pulsing period includes a plurality of pulses wherein said objects are subjected to substantially instantaneous changes in pressure from below about 5 psi to at least about atmospheric pressure.

11. A method according to claim 10 wherein said pulsing period includes at least 10 pulses and is followed by a holding period of duration at least about ½ the total duration of the pulsing period.

12. A method according to claim 11 wherein the pressure in said chamber during said holding period is at least about atmospheric.

13. A method for sterilizing objects contaminated with microorganisms comprising:
  providing a first sterilizing chamber adapted to receive an article for sterilization, said chamber being heatable, sealable and pressurizable;
  providing a second generator chamber in communication with said first sterilizing chamber through pump means and through valve means;
  placing articles to be sterilized into said first chamber;
  sealing said first chamber;
  providing a quantity of biocidal vapor including alcohol in said second chamber with said second chamber in sealed condition;
  pumping atmosphere from said first chamber thereby to create a pressure differential between the interiors of said first and second chambers;
  upon the obtention of a preselected pressure differential between said first and second chambers, operating said valve means to open communication between said chambers, thereby to permit biocidal vapors to pass from said second to said first chamber until the pressures within the said chambers are approximately equalized, and thereafter closing communication between said chambers, thereby providing sterilizing ambient conditions within said first chamber;
  operating said pump means to withdraw biocidal vapors from said first chamber and transfer them to said second chamber again to develop said preselected pressure differential;
  again operating said valve means to permit transfer of biocidal vapors from said second chamber to said first chamber to approximately equalize the pressure within said chambers, and again closing communication between said chambers;
  repeating said step of operating said pump and operating said valve for a predetermined pulsing period; and
  thereafter maintaining biocidal sterilizing conditions within said first chamber for a holding period.

14. A method according to claim 13 wherein following said holding period, the pump means and valve means are operated to circulate biocidal vapors out of and into said first chamber during a second pulsing period, and thereafter biocidal sterilizing conditions are again maintained in said first chamber during a second holding period.

15. A method according to claim 14 wherein subsequent to said first holding period and prior to said subsequent operation of the pump means and valve means, a second quantity of biocidal vapors is introduced to said second chamber.

16. A method according to claim 13 wherein said sporicidal atmosphere is produced by vaporizing a sterilizing fluid comprising formaldehyde, alcohol and water.

17. A method according to claim 16 wherein said sporicidal atmosphere is maintained at a temperature within the range of about 120° to about 140° F.

18. A method according to claim 17 wherein during said pulsing period, the pressure is caused to increase from said relatively low pressure to said relatively high pressure substantially instantaneously.

19. A method according to claim 18 wherein said low pressure is less than about 10 inches of Hg and said high pressure is at least about atmospheric.

20. A method according to claim 13 wherein said pulsing period includes a plurality of pulses wherein said objects are subjected to substantially instantaneous changes in pressure from below about 5 psi to at least about atmospheric pressure.

21. A method according to claim 20 wherein said pulsing period includes at least 10 pulses and is followed by a holding period of duration at least about ½ the total duration of the pulsing period.

22. A method according to claim 21 wherein the pressure in said chamber during said holding period is at least about atmospheric.

23. A method of sterilizing objects contaminated with microorganisms comprising:
  placing the objects in a sterilizing chamber, evacuating said chamber, and thereafter subjecting them to a sporicidal atmosphere during a sterilization cycle including a pulsing period and a holding period;
  subjecting said objects alternately to relatively low and relatively high pressure conditions through a plurality of pulses during said pulsing period, wherein the change from said low to said high pressure occurs substantially instantaneously; and
  thereafter holding said objects in said atmosphere at a relatively high pressure for a holding period, said holding period having a duration of at least about one-third the duration of said cycle.

24. A method according to claim 23 wherein said sporicidal atmosphere is maintained at a temperature within the range of about room temperature to about 160° F.; and the pressure within said sterilizing chamber during said pulsing period varies in magnitude from below about 5 psi to at least about atmospheric.

25. A method according to claim 23 including a plurality of said cycles in sequence, each said cycle including a said pulsing period followed by a said holding period.

26. A method according to claim 25 wherein each said holding period has a duration of at least about one-third the duration of the cycle including said holding period.

27. A method for sterilizing objects contaminated with microorganisms comprising:
  providing a first sterilizing chamber adapted to receive an article for sterilization, said chamber being heatable, sealable and pressurizable;
  providing a second generator chamber in communication with said first sterilizing chamber through pump means and through valve means;
  placing articles to be sterilized into said first chamber;
  sealing said first chamber;
  providing a quantity of biocidal vapor in said second chamber with said second chamber in sealed condition;
  pumping atmosphere from said first chamber thereby to establish a preselected pressure differential between the interiors of said first and second chambers;
  upon the obtention of said preselected pressure differential between said first and second chambers, operating said valve means to open communication between said chambers, thereby to subject said articles to a substantially instantaneous change in pressure of at least about 10 psi in magnitude;
  closing communication between said chambers;
  operating said pump means to withdraw biocidal vapors from said first chamber and transfer them to said second chamber again to develop said preselected pressure differential;

again operating said valve means to permit transfer of biocidal vapors from said second chamber to said first chamber, thereby again subjecting said articles to a substantially instantaneous change in pressure of at least about 10 psi in magnitude, and again closing communication between said chambers;

repeating said steps of operating said pump and operating said valve for a predetermined pulsing period; and thereafter maintaining biocidal sterilizing conditions within said first chamber for a holding period.

28. A method according to claim 27 wherein following said holding period, the pump means and valve means are operated to circulate biocidal vapors out of and into said first chamber during a second pulsing period, and thereafter biocidal sterilizing conditions are again maintained in said first chamber during a second holding period.

29. A method according to claim 28 wherein subsequent to said first holding period and prior to said subsequent operation of the pump means and valve means, a second quantity of biocidal vapors is introduced to said second chamber.

30. A method according to claim 28 wherein discrete pulses are caused to occur at a rate of at least about 10 per minute during each said pulsing period.

31. A method according to claim 32 wherein the pressure in said first chamber during each of said holding periods is at least about atmospheric.

32. A method according to claim 31 wherein a sterilization procedure includes sufficient said pulsing periods and holding periods to require at least about one hour's duration, and the duration of each said holding period is at least about one-fourth the duration of the immediately preceding pulsing period.

33. A method according to claim 27 wherein said biocidal vapor comprises formaldehyde and alcohol and is unsaturated with respect to water.

34. A method according to claim 33 wherein following said holding period, the pump means and valve means are operated to circulate biocidal vapors out of and into said first chamber during a second pulsing period, and thereafter biocidal sterilizing conditions are again maintained in said first chamber during a second holding period.

35. A method according to claim 34 wherein discrete pulses are caused to occur at a rate of at least about 10 per minute during each said pulsing period.

36. A method according to claim 35 wherein the pressure in said first chamber during each of said holding periods is at least about atmospheric.

37. A method according to claim 36 wherein a sterilization procedure includes sufficient said pulsing periods and holding periods to require at least about one hour's duration, and the duration of each said holding period is at least about one-fourth the duration of the immediately preceding pulsing period.

* * * * *